United States Patent [19]

Goto et al.

[11] Patent Number: 4,820,443
[45] Date of Patent: Apr. 11, 1989

[54] CYCLOHEXANE DERIVATIVE AND LIQUID CRYSTAL COMPOSITION CONTAINING THE SAME

[75] Inventors: Yasuyuki Goto; Tetsuya Ogawa, both of Yokohamashi, Japan

[73] Assignee: Chisso Corporation, Japan

[21] Appl. No.: 151,192

[22] Filed: Feb. 1, 1988

[30] Foreign Application Priority Data

Feb. 6, 1987 [JP] Japan .................................. 61-25683
Jul. 20, 1987 [JP] Japan ................................ 61-180238

[51] Int. Cl.$^4$ .................. G02F 1/13; C09K 19/30; C07C 19/08; C07C 25/18; C07C 121/00
[52] U.S. Cl. ............................. 252/299.63; 350/350 R; 570/129; 570/182; 558/425
[58] Field of Search ............... 252/299.63; 350/350 R; 570/129, 182; 558/425

[56] References Cited

U.S. PATENT DOCUMENTS

| | | | |
|---|---|---|---|
| 4,400,293 | 8/1983 | Romer et al. | 252/299.63 |
| 4,405,488 | 9/1983 | Sugimori et al. | 252/299.63 |
| 4,514,044 | 4/1985 | Gunjima et al. | 252/299.63 |
| 4,536,321 | 8/1985 | Sugimori et al. | 252/299.63 |
| 4,545,922 | 10/1985 | Eidenschink et al. | 252/299.63 |
| 4,551,280 | 11/1985 | Sasaki et al. | 252/299.63 |
| 4,556,745 | 12/1985 | Carr et al. | 252/299.63 |
| 4,606,845 | 8/1986 | Romer et al. | 252/299.63 |
| 4,621,501 | 11/1986 | Metrzilka et al. | 252/299.63 |
| 4,630,896 | 12/1986 | Metrzilka et al. | 252/299.63 |
| 4,637,897 | 1/1987 | Kelly | 252/299.63 |
| 4,659,502 | 9/1987 | Fearon et al. | 252/299.63 |
| 4,664,840 | 5/1987 | Osman | 252/299.63 |
| 4,695,131 | 9/1987 | Balkwill et al. | 252/299.63 |
| 4,695,398 | 9/1987 | Goto et al. | 252/299.63 |
| 4,704,005 | 11/1987 | Boller et al. | 252/299.63 |
| 4,710,315 | 12/1987 | Schad et al. | 252/299.63 |

FOREIGN PATENT DOCUMENTS

| | | | |
|---|---|---|---|
| 84194 | 7/1983 | European Pat. Off. | 252/299.63 |
| 102047 | 3/1984 | European Pat. Off. | 252/299.61 |
| 117631 | 9/1984 | European Pat. Off. | 252/299.61 |
| 125563 | 11/1984 | European Pat. Off. | 252/299.61 |
| 205998 | 12/1986 | European Pat. Off. | 252/299.61 |
| 59-16840 | 1/1984 | Japan | 252/299.63 |
| 60-84230 | 5/1985 | Japan | 252/299.63 |
| WO85/04874 | 11/1985 | PCT Int'l Appl. | 252/299.63 |
| WO86/05484 | 9/1986 | PCT Int'l Appl. | 252/299.61 |

OTHER PUBLICATIONS

Balkwill et al., "Fluorination in Nematic Systems", Mol. Cryst. Liq. Cryst., 1985, vol. 123, pp. 1-13.

*Primary Examiner*—Teddy S. Gron
*Attorney, Agent, or Firm*—Leydig, Voit & Mayer

[57] ABSTRACT

A cyclohexane derivative having a low viscosity, a broad nematic phase temperature range, a good compatibility with other liquid crystal components even at low temperatures and a large positive dielectric anisotropy value, and a liquid crystal composition containing the cyclohexane derivative are provided, which cyclohexane derivative is expressed by the formula

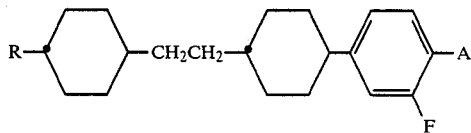

wherein R represents an alkyl group of 1-10 C and A represents a hydrogen atom, a halogen atom of F, Cl or Br or a cyano group.

5 Claims, No Drawings

CYCLOHEXANE DERIVATIVE AND LIQUID CRYSTAL COMPOSITION CONTAINING THE SAME

BACKGROUND OF THE INVENTION

1. Field of the Invention

This invention relates to a cyclohexane derivative used as a component of liquid crystal materials and a liquid crystal composition containing the same.

2. Description of the Related Art

Display devices applying liquid crystals utilize the electro-optical effect based on the anisotropies of the dielectric constant and electrical conductivity of liquid crystal substances. Liquid crystal display modes include various modes such as dynamic scattering type, twisted nematic type, phase change type, deformation of vertical aligned phase type, guest-host type, etc. Properties required for liquid crystal substances used for liquid crystal display vary depending on the respective liquid crystal display modes, but it is required in to all display modes that the substances should have a broad mesomorphic range and should be stable to moisture, air, light, heat, electricity, etc. Further, when the substances are used or liquid crystal display devices, it is also desired that the response of the display devices be quick and the devices can be driven at a voltage as low as possible. At present, however, there is no single substance which satisfies these requirements; hence actually, there have been used liquid crystalline mixtures obtained by blending several kinds of liquid crystal compounds or by blending compounds similar to liquid crystals with several kinds of liquid crystal compounds.

Recently, as the range of use of liquid crystal display has been increasing, specific features required for liquid crystal materials have also been becoming more severe. Materials useful at low temperatures have also been desired. For example, the service temperature range employed particularly for displays loaded on cars is −40° to 100° C.

SUMMARY OF THE INVENTION

An object of the present invention is to provide a compound which has a low viscosity, a positive dielectric anisotropy, a broad nematic phase temperature range, and a good compatibility with other liquid crystal components even at low temperatures.

Further, another object of the present invention is to provide a liquid crystal mixture which is capable of realizing a low threshold voltage for driving display elements and also has a low viscosity.

The present invention resides in a cyclohexane derivative expressed by the formula

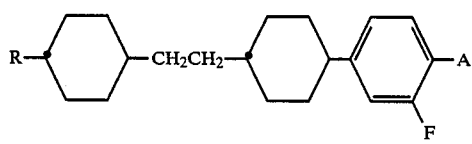

(I)

wherein R represents an alkyl group of 1 to 10 carbon atoms and A represents a hydrogen atom, a halogen atom of F, Cl or Br or a cyano group, and a liquid crystal composition containing the same.

DETAILED DESCRIPTION OF PREFERRED EMBODIMENTS

Cyclohexane derivatives expressed by the formula (I) include compounds expressed by the following formulas (a)–(e), and useful as a component of liquid crystal display materials, and R in the formulas is as defined above:

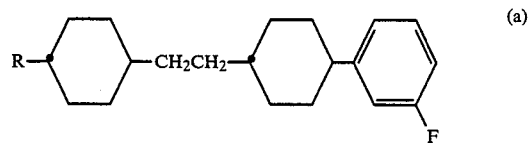

(a)

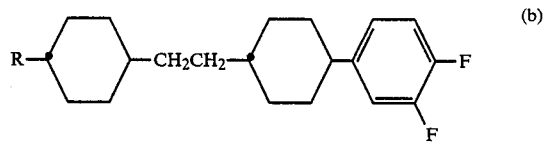

(b)

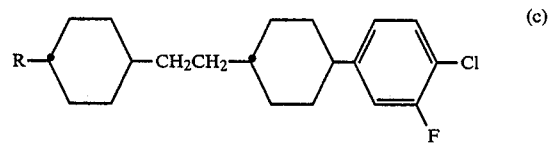

(c)

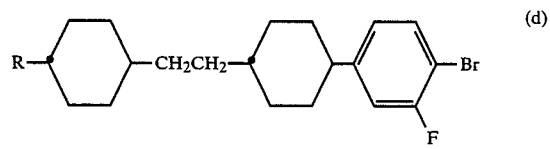

(d)

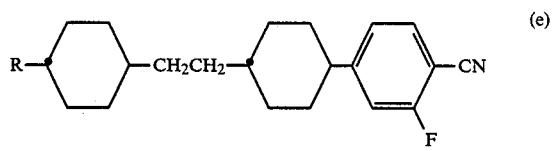

(e)

These compounds have a broad nematic phase temperature range and exhibit a positive dielectric anisotropy (hereinafter abbreviated to $\Delta\epsilon$). These compounds have a superior compatibility with other liquid crystal substances, particularly at low temperatures and the compounds expressed by the formulas (a) to (d) have a low viscosity.

The compound of the formula (e) has a higher viscosity than those of the compounds of the other formulas, but has a large positive $\Delta\epsilon$ value, and when the compound is blended with liquid crystal materials having a relatively low viscosity, it is possible to reduce the driving voltage of the resulting liquid crystal cells.

As to compounds having substituents on the end phenyl ring thereof similar to those of the compounds of the present invention, compounds expressed by the following formulas (1) and (2) are disclosed in U.S. Pat. Nos. 4,405,488 and 4,536,321. Further, compounds of the following formulas (3) and (4) also similar in the core structure to the compounds of the present invention are disclosed in International Patent Application laid-open No. WO 85/04874:

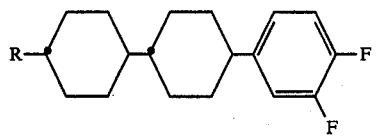  (1)

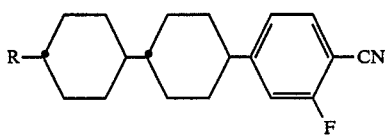  (2)

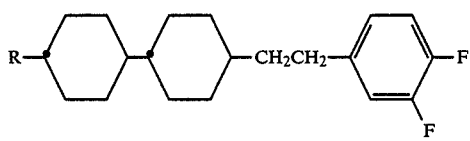  (3)

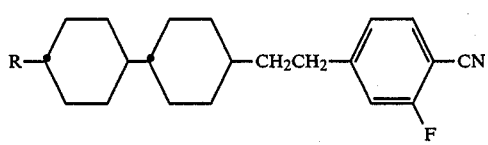  (4)

In the above formulas, R represents a linear chain alkyl group.

Comparison of these compounds with those of the present invention will be described later in Comparative test.

The compounds of the present invention not only have a specific feature of good compatibility with other liquid crystals at low temperatures, but also have well-balanced specific features preferred as a liquid crystal component, such as low viscosity, broad nematic range and absence of smectic phase or an extremely narrow range of smectic phase, if any.

Next, an embodiment of preparation of the cyclohexane derivative of the present invention will be described. The compounds of the formulas (a), (b), (c) and (d) may be prepared according to the following equations:

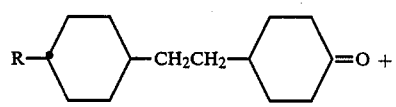

(II)

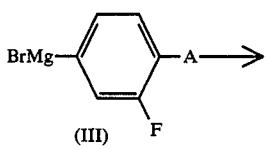

(III)

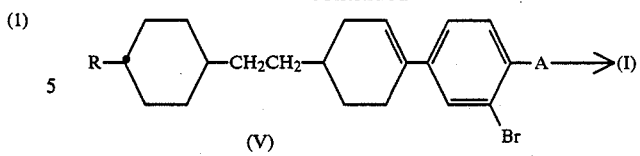

(IV)

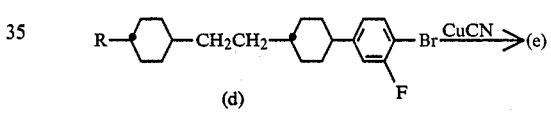

(V)

Namely, a ketone expressed by the formula (II) is reacted with a Grignard reagent (III) obtained from a 3-fluoro-4-substituted-bromobenzene (or 3-fluoro-bromobenzene) and metal magnesium to yield an alcohol derivative of the formula (IV), which is then subjected a dehydration reaction in the presence of a catalyst mentioned later in an inert organic solvent at a suitable reflux temperature of the solvent under the atmospheric pressure to obtain a cyclohexane derivative of the formula (V). As the inert organic solvent, benzene, toluene, chloroform, carbon tetrachloride, methylene chloride, etc. are suitable and as the catalyst, Lewis acids such as aluminum chloride, tin tetrachloride, toluenesulfonic acid, etc. or mineral acids such as sulfuric acid, phosphoric acid, hydrochloric acid, etc. may be used. Successively, the compound (V) is subjected to catalytic reduction reaction, followed by subjecting the reaction material to a suitable purification treatment to isolate the objective compound (I). Further, the compound (e) may be prepared by reacting cuprous cyanide with the compound (d) in a suitable basic solvent or according to a known reaction using the compound (a) as raw material.

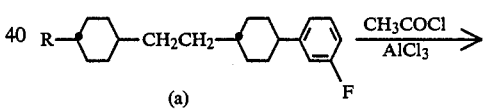

(d)

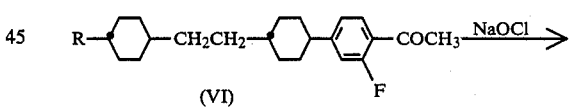

(a)

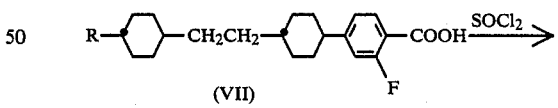

(VI)

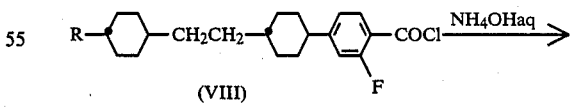

(VII)

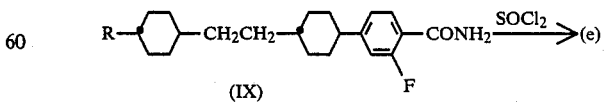

(VIII)

R—◯—CH$_2$CH$_2$—◯—⌬—CONH$_2$ $\xrightarrow{SOCl_2}$ (e)

(IX)   F

Namely, the above compound (a) as a starting raw material is converted into a ketone compound (VI) by a Friedel-Crafts synthesis, which is converted into a carboxylic acid (VII) by a haloform reaction, which is chlorinated into an acid chloride (VIII), which is converted into an amide compound (IX), which is dehydrated to obtain a compound (e).

The liquid crystal mixture of the present invention in the second aspect comprises at least two liquid crystalline compounds at least one of which is a liquid crystal compound expressed by the formula (I).

As compounds used in admixture with the compound of the formula (I), as a component of the liquid crystal composition of the present invention, a group of known compounds expressed by the following formulas (i) to (xxxiii) may be illustrated:

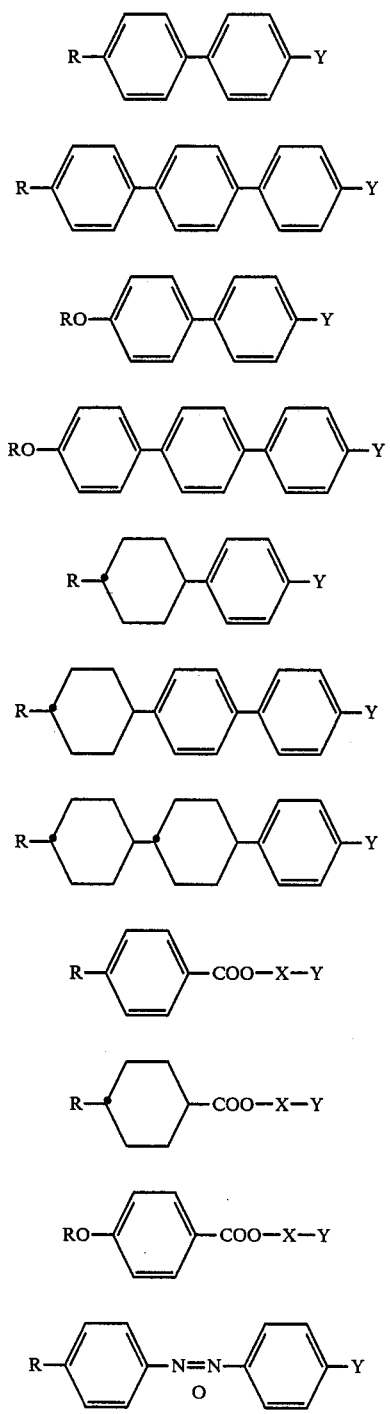

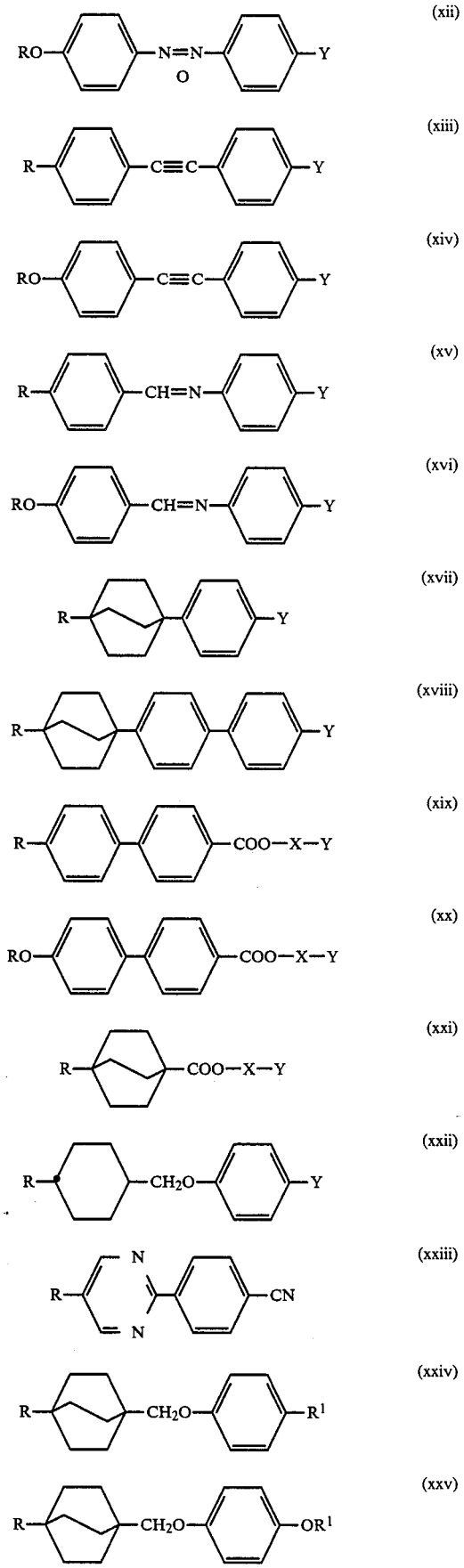

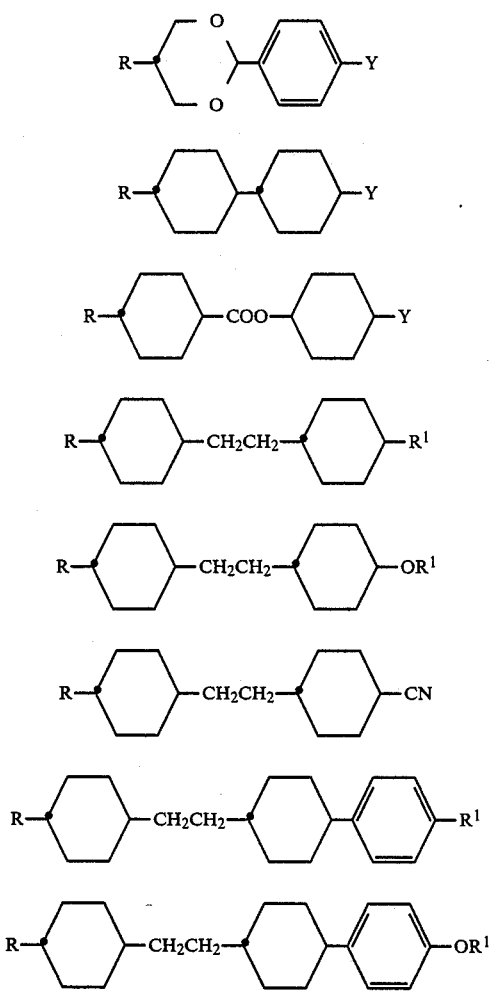

In the above formulas (i)–(xxxiii), X represents

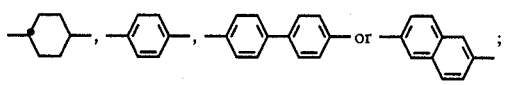

Y represents —CN, halogen atom, R¹ or —OR¹; and R and R¹ each represent an alkyl group.

The present invention will be described in more detail by way of examples, but it should not be construed to be limited thereto.

Further, in the examples, the C-N point and N-I point represent crystalline-nematic phase transition point and nematic-isotropic liquid phase transition point, respectively.

EXAMPLE 1

[Trans-4'-(trans-4''-propylcyclohexylethyl)cyclohexyl]-3,4-difluorobenzene 4-(Trans-4'-propylcyclohexylethyl)cyclohexanone (25 g, 0.1 mol) was added to a solution of a Grignard reagent prepared from 3,4-difluorobromobenzene (27.3 g, 0.1 mol) and magnesium (2.43 g, 0.1 mol) in tetrahydrofuran (100 ml), at 10° C., followed by reacting at 50° C. for 3 hours, allowing the reaction mixture to cool down to room temperature, adding 6N-hydrochloric acid (50 ml) and water (200 ml) thereto, extracting the resulting freed oily substance with n-heptane (100 ml), washing the extract with deionized water till the water became neutral, distilling off n-heptane to obtain an oily substance corresponding to [trans-4'-(trans-4''-propylcyclohexylethyl)-1'-hydroxycyclohexyl]-3,4-difluorobenzene, adding to this oily substance, p-toluenesulfonic acid (1 g) and toluene (200 ml), heating the mixture under reflux, removing water formed, allowing the resulting toluene solution to cool down to room temperature after completion of the reaction, washing it with water till the washing water became neutral, drying with anhydrous sodium sulfate, distilling off toluene and recrystallizing the remaining solids from ethyl acetate (50 ml) to obtain [trans-4'-(trans-4''-propylcyclohexylethyl)-1'-cyclohexen-1'-yl]-3,4-difluorobenzene (22.9 g). This product exhibited phase transition points of C-N point 36.4° C. and N-I point 87.1°.

This cyclohexene derivative was dissolved in ethyl acetate (200 ml), followed by adding developed Raney nickel (5.0 g) to carry out a catalytic reduction reaction at 25° C. under atmospheric pressure until hydrogen absorption ceased, thereafter filtering off Raney nickel, distilling off ethyl acetate from the filtrate and twice recrystallizing the remaining oily substance from n-hexane to obtain the objective compound, [trans-4'-(trans-4''-propylcyclohexylethyl)cyclohexyl]-3,4-difluorobenzene (11.9 g). This product exhibited as broad a nematic temperature range as between 33.3° C. (C-N point) and 104.3° C. (N-I point). Its viscosity (extrapolated value at 20° C.) was as low as 18 cp.

Further, the elemental analysis values of the product accorded well with the calculated values.

|  | C | H |  |
|---|---|---|---|
| Calculated value (%) | 79.26 | 9.83 | (in terms of $C_{23}H_{34}F_2$) |
| Analytical value (%) | 79.41 | 9.92 |  |

EXAMPLES 2–6

The following compounds were obtained in the same manner as in Example 1:

[trans-4'-(trans-4''-ethylcyclohexylethyl)cyclohexyl]-3,4-difluorobenzene

C-N point: 27.3° C., N-I point: 73.7° C.

[trans-4'-(trans-4''-butylcyclohexylethyl)cyclohexyl]-3,4-difluorobenzene

C-N point: 31.5° C., N-I point: 102.9° C.

[trans-4'-(trans-4''-pentylcyclohexylethyl)cyclohexyl]-3,4-difluorobenzene

C-N point: 36.8° C., N-I point: 110.4° C.

[trans-4'-(trans-4''-ethylcyclohexylethyl)cyclohexyl]-3-fluoro-4-chlorobenzene

C-N point: 39.6° C., N-I point: 103.7° C.

[trans-4'-(trans-4''-propylcyclohexylethyl)cyclohexyl]-3-fluoro-4-chlorobenzene

C-N point: 59.0° C., N-I point: 132.0° C.

EXAMPLE 7

2-Fluoro-4-[trans-4'-(trans-4''-propylcyclohexylethyl)cyclohexyl]benzonitrile (i) 3-[Trans-4'-(trans-4''-propylcyclohexylethyl)cyclohexyl]fluorobenzene (C-N point: 48.4° C., N-I point: 79.4° C.) (50 g) obtained from 3-fluorobromobenzene and 4-(trans-4'-propylcyclohexylethyl)cyclohexanone in the same manner as in Example 1, was dissolved in nitrobenzene (100 cc), followed by adding anhydrous aluminum chloride (50.5 g) to the solution, agitating it, dropwise adding acetyl chloride (29 g) to the mixture, heating the resulting mixture on a water bath at 40° C. for 2 hours after completion of heat generation to complete reaction, adding the reaction material to a mixture of ice (500 g) with conc. hydrochloric acid (100 cc), vigorously agitating the mixture to decompose the resulting aluminum chloride complex, extracting the freed oily substance with toluene (200 cc), washing the extract solution with water until the wash water became neutral, drying it over anhydrous sodium sulfate, filtering off the drying agent, distilling off toluene and nitrobenzene and recrystallizing a remaining oily substance from ethyl acetate to obtain 2-fluoro-4-[trans-4'-(trans-4''-propylcyclohexylethyl)cyclohexyl]acetophenone (20.2 g). This product exhibited a liquid crystal phase over 62.1° C. (C-N point) to 161.4° C. (N-I point).

(ii) 2-Fluoro-4-[trans-4'-(trans-4''-propylcyclohexylethyl)cyclohexyl]acetophenone (10 g) obtained in the above paragraph (i) was dissolved in dioxane (100 cc), followed by adding an aqueous solution of sodium hypobromite prepared from bromine (17 g) and sodium hydroxide (19 g), reacting the mixture at 50° C. for 4 hours, allowing the resulting material to cool down after completion of the reaction, adding 6N hydrochloric acid (100 cc), filtering off the deposited mass, drying and recrystallizing from acetic acid (160 cc) to obtain acicular 2-fluoro-4-[trans-4'-(trans-4''-propylcyclohexylethyl)cyclohexyl]benzoic acid (8.2 g) (m.p. higher than 250° C.).

(iii) 2-Fluoro-4-[trans-4'-(trans-4''-propylcyclohexylethyl)cyclohexyl]benzoic acid obtained as described in the above paragraph (ii) was reacted with thionyl chloride to obtain an acidic chloride (5 g), which was dissolved in dioxane (20 cc), followed by adding the solution to a mixture of ice (100 g) with aqueous ammonia (38% solution) (30 cc), vigorously agitating the mixture, filtering off the deposited mass and drying the mass to obtain an acid amide compound (4.5 g).

(iv) Toluene (50 cc) and thionyl chloride (50 cc) were added to the acid amide (4.5 g) obtained as described in the above paragraph (iii), followed by reacting the mixture under reflux on heating for 10 hours, allowing the resulting material to cool down after completion of the reaction, adding it to ice (100 g), agitating the mixture, separating the toluene layer, washing it with a dilute alkali aqueous solution, further washing with water until the wash water became neutral, drying the toluene solution over anhydrous sodium sulfate, filtering off the drying agent, distilling off toluene from the toluene solution and recrystallizing the remaining solids from ethyl acetate to obtain the objective 2-fluoro-4-[trans-4'-(trans-4''-propylcyclohexylethyl)cyclohexyl]benzonitrile (2.2 g).

This product exhibited as broad a liquid crystal phase as between 64.2° C. (C-N point) and 169.6° C. (N-I point).

EXAMPLES 8 AND 9

The following compounds were obtained in the same manner as in Example 7:

2-Fluoro-4-[trans-4''-(trans-4''-ethylcyclohexylethyl)-cyclohexyl]benzonitrile
C-N point: 70.6° C., N-I point: 145.6° C.
2-Fluoro-4-[trans-4'-(trans-4''-butylcyclohexylethyl)cyclohexyl]benzonitrile
C-N point: 54.9° C., N-I point: 165.7° C.

USE EXAMPLE 1

A liquid crystal composition (A) consisting of
trans-4-propyl-(4-cyanophenyl)cyclohexane 30% by weight,
trans-4-pentyl-(4-cyanophenyl)cyclohexane 40% by weight and
trans-4-heptyl-(4-cyanophenyl)cyclohexane 30% by weight
has a N-I point of 52.1° C., a dielectric anisotropy value ($\Delta\epsilon$) of 10.7 and a viscosity at 20° C. of 22.4 cp. This composition was placed in a TN type cell of 10 μm thickness and its characteristics were measured to give a threshold voltage of 1.57 V and a saturation voltage of 2.13 V.

To this liquid crystal composition (A) (85 parts by weight) was added [trans-4'''-(trans-4''-propylcyclohexylethyl)cyclohexyl]-3,4-difluorobenzene (15 parts by weight) obtained in Example 1 to prepare a liquid crystal composition. The N-I point rose to 58.0° C. Its $\Delta\epsilon$ was 10.1. The viscosity at 20° C. was lowered to 21.1 cp. That is, it is seen that the viscosity-reducing effect of the compound of the present invention is superior. When this composition was placed in the above-mentioned TN cell, the resulting element exhibited a threshold voltage of 1.52 V and a saturation voltage of 2.36 V.

USE EXAMPLE 2

To the liquid crystal composition (A) (85 parts by weight) used in Use Example 1 was added [trans-4'-(trans-4''-ethylcyclohexylethyl)cyclohexyl]-3,4-difluorobenzene (15 parts by weight) obtained in Example 2 to prepare a liquid crystal composition. The N-I point rose to 54.1° C. The $\Delta\epsilon$ was 10.0. The viscosity at 20° C. was lowered to 21.0 cp. Further, this liquid crystal composition was placed in the above-mentioned TN cell. The resulting element exhibited a threshold voltage of 1.52 V and a saturation voltage of 2.36 V.

USE EXAMPLE 3

To the liquid crystal composition (A) (85 parts by weight) used in Use Example 1 was added [trans-4'-(trans-4''-butylcyclohexylethyl)cyclohexyl]-3,4-difluorobenzene (15 parts by weight) to obtain a liquid crystal composition, which exhibited a N-I point of 56.7° C., a $\Delta\epsilon$ of 10.2 and a viscosity at 20° C. of 22.0 cp. Further this liquid crystal composition was placed in the above-mentioned TN cell. The resulting element exhibited a threshold voltage of 1.53 V and a saturation voltage of 2.47 V.

USE EXAMPLE 4

2-Fluoro-4-[trans-4'-(trans-4''-propylcyclohexylethyl)cyclohexyl]benzonitrile (15 parts by weight) was added to the liquid crystal composition (A) (85 parts by weight) used in Use Example 1 to obtain a liquid crystal composition, which exhibited a N-I point of 62.5° C., a $\Delta\epsilon$ of 11.3 and a viscosity at 20° C. of 24.4 cp. Further, when this liquid crystal composition was filled in the above-mentioned TN cell, the resulting threshold voltage and saturation voltage were 1.52 V and 2.30 V, respectively.

COMPARATIVE TEST

To the respective compounds of the above-mentioned formulas (1), (2), (3) and (4) wherein R represents n-$C_3H_7$ (each 15 parts by weight) was added the liquid crystal composition (A) (85 parts by weight) shown in Use Example 1 to prepare liquid crystal compositions (1), (2), (3) and (4), respectively. These liquid crystal compositions and the liquid crystal compositions of the present invention prepared in Use Examples 1 and 4 were allowed to stand in a freezer at −40° C. for 30 days to observe the presence or absence of crystal deposition and examine their low temperature compatibilities. The results and viscosities at 20° C. (abbreviated to $\eta_{20}$) together with phase transition points of the respective compounds (15 parts by weight) added to the composition (A) (85 parts by weight) are shown in Table 1.

component, a nematic liquid crystal mixture having a low viscosity is obtained.

What we claim is:

1. A cyclohexane derivative expressed by the formula

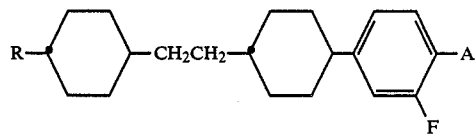

TABLE 1

| Composition No. | Added compound | Phase transition point (°C.) C | S | N | I | $\eta_{20}$ (cp) | Low temp. compatibility |
|---|---|---|---|---|---|---|---|
| (1) | n-C$_3$H$_7$–[Cy]–[Cy]–[Ph(3,4-diF)] | • 44.2 | — | • 118.0 | • | 22.5 | x |
| (2) | n-C$_3$H$_7$–[Cy]–[Cy]–[Ph(3-F,4-CN)] | • 53.8 | • 90.0 | • 207.0 | • | 27.1 | x |
| (3) | n-C$_3$H$_7$–[Cy]–[Cy]–CH$_2$CH$_2$–[Ph(3,4-diF)] | • 18.4 | • 49.5 | • 118.3 | • | 22.3 | x |
| (4) | n-C$_3$H$_7$–[Cy]–[Cy]–CH$_2$CH$_2$–[Ph(3-F,4-CN)] | • 72.1 | — | • 172.9 | • | 25.0 | x |
| Use 1 | n-C$_3$H$_7$–[Cy]–CH$_2$CH$_2$–[Cy]–[Ph(3,4-diF)] | • 33.3 | — | • 104.3 | • | 21.7 | o |
| Use 4 | n-C$_3$H$_7$–[Cy]–CH$_2$CH$_2$–[Cy]–[Ph(3-F,4-CN)] | • 62.1 | — | • 161.4 | • | 24.4 | o |
| — | Liquid crystal composition (A) | • −18 | — | • 52.1 | • | 22.4 | x |

(Note)
In Table 1, C, S, N and I in the column of phase transition point represent the respective phases of crystal, smectic, nematic and isotropic liquid. The symbols • and — in the lower column mean the presence or absence of phases shown in the paragraph thereabove. The symbols x and o in the paragraph of low temperature compatibility indicate the presence and absence of crystal deposition, respectively.

From the results of this Comparative test, it is seen that the compounds of the present invention is superior in low temperature compatibility and the lower limit temperature of the nematic phase of alkylcyclohexylbenzonitrile liquid crystal mixture can be lowered.

As apparent from the foregoing, the present invention provides a low viscosity liquid crystal having a large positive dielectric anisotropy value and also a good compatibility with existing liquid crystal compounds. Further, using the liquid crystal compound as a wherein R represents an alkyl group of 1 to 10 carbon atoms and A represents a hydrogen atom, a halogen atom of F, Cl or Br or a cyano group.

2. A cyclohexane derivative according to claim 1, expressed by the formula

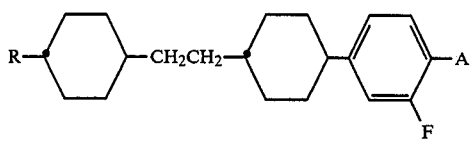

wherein R represents an alkyl group of 1 to 10 carbon atoms.

3. A cyclohexane derivative according to claim 1, expressed by the formula

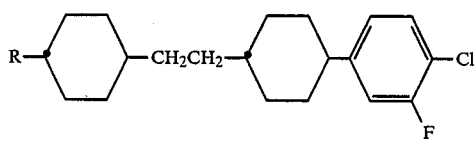

wherein R represents an alkyl group of 1 to 10 carbon atoms.

4. A cyclohexane derivative according to claim 1, expressed by the formula

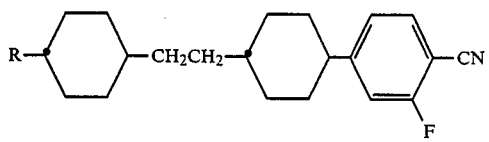

wherein R represents an alkyl group of 1 to 10 carbon atoms.

5. A liquid crystal composition comprising at least two components at least one of which is a cyclohexane derivative expressed by the formula

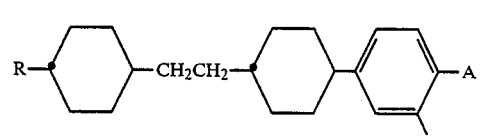

wherein R represents an alkyl group of 1 to 10 carbon atoms and A represents a hydrogen atom, a halogen atom of F, Cl or Br or a cyano group.

* * * * *

UNITED STATES PATENT AND TRADEMARK OFFICE
CERTIFICATE OF CORRECTION

PATENT NO. : 4,820,443
DATED : April 11, 1989
INVENTOR(S) : Goto et al

It is certified that error appears in the above-identified patent and that said Letters Patent is hereby corrected as shown below:

Title Page:
In the listing of the Foreign Application Priority Data please change "61-25683" and "61-180238" to --62-25683-- and --62-180238-- respectively.

In column 5, line 65, change "R-⟨⟩-N=N-⟨⟩-Y" to
--R-⟨⟩-N=N-⟨⟩-Y--.
           O

In column 6, line 2, change "RO-⟨⟩-N=N-⟨⟩-Y" to
--RO-⟨⟩-N=N-⟨⟩-Y--.
            O Signed and Sealed this Twenty-fourth Day of July, 1990

Attest:

HARRY F. MANBECK, JR.

Attesting Officer

Commissioner of Patents and Trademarks